(12) United States Patent
Schmidt et al.

(10) Patent No.: US 6,753,150 B2
(45) Date of Patent: Jun. 22, 2004

(54) METHOD FOR DETERMINING WHETHER A COMPOUND IS CAPABLE OF INHIBITING THE INTERACTION OF A PEPTIDE WITH RAGE

(75) Inventors: Ann Marie Schmidt, Franklin Lakes, NJ (US); David Stern, Great Neck, NY (US)

(73) Assignee: The Trustees of Columbia University in the City of New York, New York, NY (US)

( * ) Notice: Subject to any disclaimer, the term of this patent is extended or adjusted under 35 U.S.C. 154(b) by 15 days.

(21) Appl. No.: 09/166,649

(22) Filed: Oct. 5, 1998

(65) Prior Publication Data

US 2003/0087302 A1 May 8, 2003

(51) Int. Cl.[7] .......................... G01N 33/53; C07K 17/00
(52) U.S. Cl. ................... 435/7.1; 530/350; 530/388.22; 530/387.3
(58) Field of Search .................. 530/350, 388.22, 530/402; 435/7.1, 501

(56) References Cited

U.S. PATENT DOCUMENTS 5,864,018 A * 1/1999 Morser et al. ........... 530/387.1

FOREIGN PATENT DOCUMENTS

WO     WO 97/26913    *   7/1997

OTHER PUBLICATIONS

Reddy et al., N–(Carboxymethyl)lysine is a Dominant Advanced Glycation End Product (AGE) Antigen in Tissue Proteins, Biochemistry, vol. 43, pp. 10872–10878, 1995.*

\* cited by examiner

*Primary Examiner*—Lorraine Spector
*Assistant Examiner*—Eileen B. O'Hara
(74) *Attorney, Agent, or Firm*—John P. White; Cooper & Dunham LLP

(57) ABSTRACT

The present invention provides a method for determining whether a compound is capable of inhibiting the interaction of a peptide with receptor for advanced glycation end product (RAGE), which comprises: (a) admixing: (i) the peptide, wherein amino groups of the peptide are inactivated by derivitization, (ii) RAGE or a fragment thereof, and (iii) the compound; (b) determining the amount of the peptide bound to RAGE or the fragment thereof, and (c) comparing the amount of bound peptide determined in step (b) with the amount determined when the peptide is admixed with RAGE or a fragment thereof in the absence of the compound, thereby determining whether the compound is capable of inhibiting the interaction of the peptide with RAGE or a fragment thereof, wherein a reduction in the amount of binding in the presence of the compound indicates that the compound is capable of inhibiting the interaction. The present invention also provides a method for inhibiting the interaction of an advanced glycation endproduct (AGE) with a receptor for advanced glycation endproduct (RAGE) in a subject which comprises administering to the subject a pharmaceutically acceptable amount of the compound identified in aforementioned screening method effective to inhibit the interaction between the AGE and the RAGE in the subject. The present invention also provides for a compound identified by the screening method and which is useful for the treatment of diabetes in a subject.

15 Claims, 9 Drawing Sheets

FIG. 8A
FIG. 8B
FIG. 8C

FIG. 9A
FIG. 9B

METHOD FOR DETERMINING WHETHER A COMPOUND IS CAPABLE OF INHIBITING THE INTERACTION OF A PEPTIDE WITH RAGE

The invention disclosed herein was made with Government support under NIH Grant No. AG00602 from the U.S. Department of Health and Human Services. Accordingly, the U.S. Government has certain rights in this invention.

BACKGROUND OF THE INVENTION

Throughout this application, various publications are referenced by author and date within the text. Full citations for these publications may be found listed alphabetically at the end of the specification immediately preceding the claims. The disclosures of these publications in their entireties are hereby incorporated by reference into this application in order to more fully describe the state of the art as known to those skilled therein as of the date of the invention described and claimed herein.

The products of glycation and oxidation of proteins, Advanced Glycation Endproducts (AGEs), are an heterogeneous group of structures that accumulate in settings such as aging, diabetes, and renal failure (1–2). It has been reported that AGEs may form in euglycemic inflammatory environments, driven by the myeloperoxidase pathway (3). AGEs have been linked to alterations of cellular properties, including those eventuating in impaired cellular integrity and barrier properties; mediated, for example, by progressive glycoxidation and cross-linking of critical structural proteins. In addition, AGEs interact with specific cell surface binding sites to modulate cellular properties in a manner linked to activation of proinflammatory cell signalling pathways, especially those responsive to enhanced cellular oxidant stress. While a number of cell surface interaction sites for AGEs have been identified, the best-characterized cellular interaction site for AGEs is the Receptor for AGE (RAGE), a member of the immunoglobulin superfamily (4–9). Ligation of RAGE by AGEs perturbs cellular properties resulting in the generation of an environment conducive to the development of vascular lesions, as well as exaggerated proinflammatory host responses which may contribute to the complications that ensue in disorders such as diabetes (10–23).

SUMMARY OF THE INVENTION

The present invention provides a method for determining whether a compound is capable of inhibiting the interaction of a peptide with receptor for advanced glycation end product (RAGE), which comprises: (a) admixing: (i) the peptide, wherein amino groups of the peptide are inactivated by derivitization, (ii) RAGE or a fragment thereof, and (iii)the compound; (b) determining the amount of the peptide bound to RAGE or the fragment thereof, and (c) comparing the amount of bound peptide determined in step (b) with the amount determined when the peptide is admixed with RAGE or a fragment thereof in the absence of the compound, thereby determining whether the compound is capable of inhibiting the interaction of the peptide with RAGE or a fragment thereof, wherein a reduction in the amount of binding in the presence of the compound indicates that the compound is capable of inhibiting the interaction. The present invention also provides a method for inhibiting the interaction of an advanced glycation endproduct (AGE) with a receptor for advanced glycation endproduct (RAGE) in a subject which comprises administering to the subject a pharmaceutically acceptable amount of the compound identified in aforementioned screening method effective to inhibit the interaction between the AGE and the RAGE in the subject. The present invention also provides for a compound identified by the screening method and which is useful for the treatment of diabetes in a subject.

Figure 1:
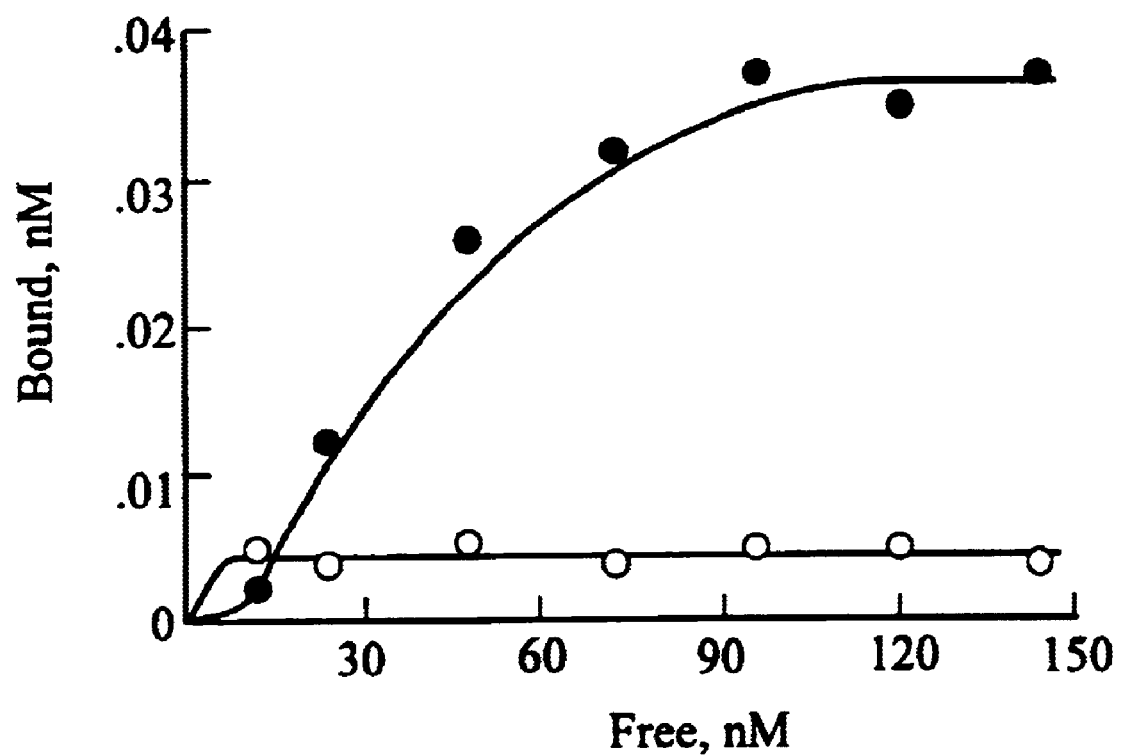
FIG. 1. Radioligand binding studies: dose response experiments. CML- or pentosidine BSA (5 µg) was immobilized to plastic wells and radioligand binding assays performed with increasing concentrations of purified $^{125}$-I sRAGE +/− excess unlabelled sRAGE (50-fold molar excess). Bound tracer was eluted with buffer containing NP40 (1%) and NaCl (0.15M) and the data subjected to analysis as described in the Experimental Details section. Only CML-BSA (closed circles) bound specifically to sRAGE ($K_D \approx 76 \pm 3.7$ nM). Pentosidine BSA exhibited no specific binding to sRAGE (open circles).

FIGS. 8A–8C. Immunohistochemistry of human diabetic kidney. Affinity-purified antibodies to CML- and pentosidine- were prepared as described above. Kidney tissue was obtained from diabetic human subjects and immunohistochemistry performed as described above: FIG. 8A: pentosidine was noted in interstitial collagens; FIG. 8B. CML epitopes were noted in basement membranes and nodules; FIG. 8C: RAGE was highly upregulated in diabetic podocytes. Controls with preimmune IgG were negative. Staining in nondiabetic kidney was minimal.

FIGS. 9A–9B. Immunohistochemistry of human kidney (active lupus nephritis). CML epitopes, FIG. 9A, were evident in the proliferative glomerular lesions and crescents in kidney tissue from a human subject with active lupus nephritis. Increased expression of RAGE, FIG. 9B, was noted in the podocytes.

DETAILED DESCRIPTION OF THE INVENTION

The following abbreviations are used herein: CML-carboxymethyl-lysine; AGE—advanced glycation endproduct(s); RAGE—receptor for advanced glycation endprocut(s); sRAGE—soluble receptor for advanced glycation endproduct(s).

The present invention provides a method for determining whether a compound is capable of inhibiting the interaction of a peptide with receptor for advanced glycation end product (RAGE), which comprises: (a) admixing: (i) the peptide, wherein amino groups of the peptide are inactivated by derivitization, (ii) RAGE or a fragment thereof, and (iii) the compound; (b) determining the amount of the peptide bound to RAGE or the fragment thereof, and (c) comparing the amount of bound peptide determined in step (b) with the amount determined when the peptide is admixed with RAGE or a fragment thereof in the absence of the compound, thereby determining whether the compound is capable of inhibiting the interaction of the peptide with RAGE or a fragment thereof, wherein a reduction in the amount of binding in the presence of the compound indicates that the compound is capable of inhibiting the interaction.

The present invention provides a screening method for identifying a compound capable of inhibiting interaction of a peptide with receptor for advanced glycation end product (RAGE), which comprises: (a) admixing: (i) the peptide, wherein amino groups of the peptide are inactivated by derivitization, (ii) RAGE or a fragment thereof, and (iii) the compound; (b) determining the amount of the peptide bound to RAGE or the fragment thereof, and (c) comparing the amount of bound peptide determined in step (b) with the amount determined in the absence of the compound, thus identifying the compound as capable of inhibiting the interaction of the peptide with RAGE.

In one embodiment, the peptide is an advanced glycation endproduct (AGE) or fragment thereof. In another embodiment, the peptide is a carboxymethyl-modified peptide. For example, peptide may be a carboxymethyl-lysine-modified AGE. In another embodiment, the peptide is a synthetic peptide.

As used herein "RAGE or a fragment thereof" encompasses a peptide which has the full amino acid sequence of RAGE as shown in Neeper et al. (1992) or a portion of that amino acid sequence. The "fragment" of RAGE is at least 5 amino acids in length, preferably more than 7 amino acids in length, but is less than the full length shown in Neeper et al. (1992). In one embodiment, the fragment of RAGE comprises the V-domain, which is a 120 amino acid domain depicted in Neeper et al. (1992). For example, the fragment of RAGE may have the amino acid sequence of the V-domain sequence of RAGE.

In one embodiment of the screening method, the inactivation by derivitization of the peptide is via chemical modification. One peptide derivative of step (a)(i) comprises an aryl derivative and one example of the aryl derivative comprises a benzoyl derivative. Another peptide derivative of step (a)(i) comprises an alkyl derivitive and an example of the alkyl derivative comprises an acetyl derivative, a propyl derivative, an isopropyl derivative, a butyl derivative, an isobutyl derivative, or a carboxymethyl derivative.

In one embodiment, the RAGE or fragment thereof of step (a)(ii) of the screening method aforementioned is synthetic.

In another embodiment, the compound has a net negative charge or a net positive charge. In a further embodiment, the compound comprises a fragment of naturally occuring soluble receptor for advanced glycation endproduct (sRAGE).

The compound identified by the screening method may comprise a variety of types of compounds. For example, in one embodiment the compound is a peptidomimetic. In another embodiment, the compound is an organic molecule. In a further embodiment, the compound is a polypeptide, a nucleic acid, or an inorganic chemical. Further, the compound is a molecule of less than 10,000 daltons. In another embodiment, the compound is an antibody or a fragment thereof. The antibody may be a polyclonal or monoclonal antibody. Furthermore, the antibody may be humanized, chimeric or primatized. In another embodiment, compound is a mutated AGE or fragment thereof or a mutated RAGE or a fragment thereof.

The screening method may be carried out in vitro, wherein one or more of the components are attached or affixed to a solid surface, or wherein the components in step a are admixed inside of a cell; or wherein the components of step (a) are admixed inside of an organism (i.e. a transgenic mouse). For example, the peptide may be affixed to a solid surface. The RAGE or the fragment thereof is affixed to a solid surface in another embodiment.

In one embodiment, the peptide is detectably labeled. In another embodiment, the RAGE or the fragment thereof is detectably labeled. The detectable label comprises fluorescence, biotin, or radioactivity.

In another embodiment of the screening method, the admixing of step (a) occurs in a cell. In another embodiment of the screening method, the admixing of step (a) occurs in an animal. For example, the animal is a transgenic animal which overexpresses RAGE or a transgenic animal which does not express RAGE.

The present invention also provides a method for inhibiting the interaction of an advanced glycation endproduct (AGE) with a receptor for advanced glycation endproduct (RAGE) in a subject which comprises administering to the subject a pharmaceutically acceptable amount of the compound identified in aforementioned screening method effective to inhibit the interaction between the AGE and the RAGE in the subject.

In one example, the subject is a human, a primate, a mouse, a rat or a dog. In another example, the administration comprises intralesional, intraperitoneal, intramuscular or intravenous injection; infusion; liposome-mediated delivery; or topical, nasal, oral, ocular or otic delivery. In a further example, the compound is administered hourly, daily, weekly, monthly or annually. In another example, the effective amount of the compound comprises from about 0.000001 mg/kg body weight to about 100 mg/kg body weight.

In one embodiment, the subject is suffering from kidney failure. In another embodiment, the subject is suffering from diabetes. In a further embodiment, the subject is suffering from systemic lupus erythematosus or inflammatory lupus nephritis. In another embodiment, the subject is an obese subject (for example, is beyond the height/weight chart recommendations of the American Medical Association). In another embodiment, the subject is an aged subject (for example, a human over the age of 50, or preferably over the age 60). In another embodiment, the subject is suffering from amyloidoses. In a further embodiment, the subject is suffering from inflammation.

In another embodiment, the method for inhibiting the interaction of an advanced glycation endproduct (AGE) with a receptor for advanced glycation endproduct (RAGE) in a subject further comprises administering to the subject a pharmaceutically acceptable carrier during the administration of the compound.

In one embodiment, the carrier comprises a diluent. In another embodiment, the carrier comprises, a virus, a liposome, a microencapsule, a polymer encapsulated cell or a retroviral vector. In another embodiment, the carrier is an aerosol, intravenous, oral or topical carrier. For example, the compound is administered from a time release implant.

The present invention also provides for a compound identified by the screening method and which is useful for the treatment of diabetes in a subject. The present invention also provides for a compound identified by the screening method and which is useful for the treatment of systemic lupus erythematosus or inflammatory lupus nephritis in a subject. The present invention also provides for a compound identified by the screening method and which is useful for the treatment of amyloidoses in a subject. The present invention provides for a compound identified by the screening method and which is useful for the treatment of inflammation in a subject. In addition, the present invention provides for a previously unknown compound identified by the aforementioned screeening method.

Figure 3:
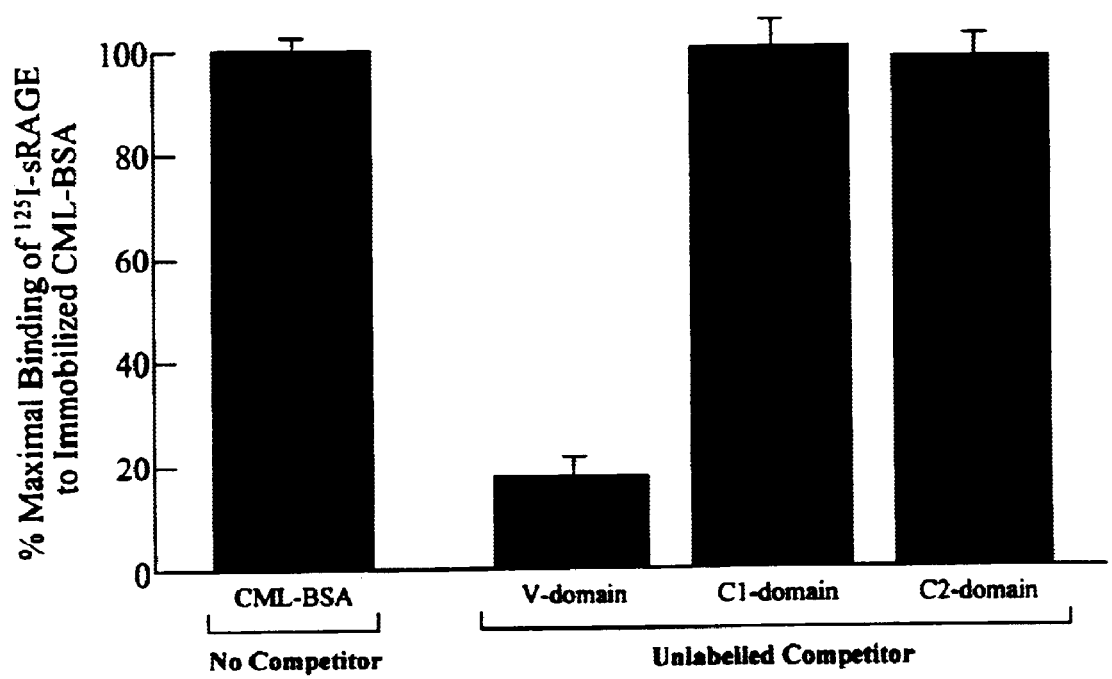
FIG. 3. Radioligand binding studies: CML-adducts interact with the V-type Ig domain of RAGE. CML-BSA was immobilized to wells; binding was performed with $^{125}$-I sRAGE (100 nM) in the presence or absence of excess unlabelled (100-fold) V-type Ig domain, C1 Ig domain or C2 Ig domain. Percent maximal binding is reported compared to binding to immobilized CML-BSA without competitor (100%).
Figure 4:
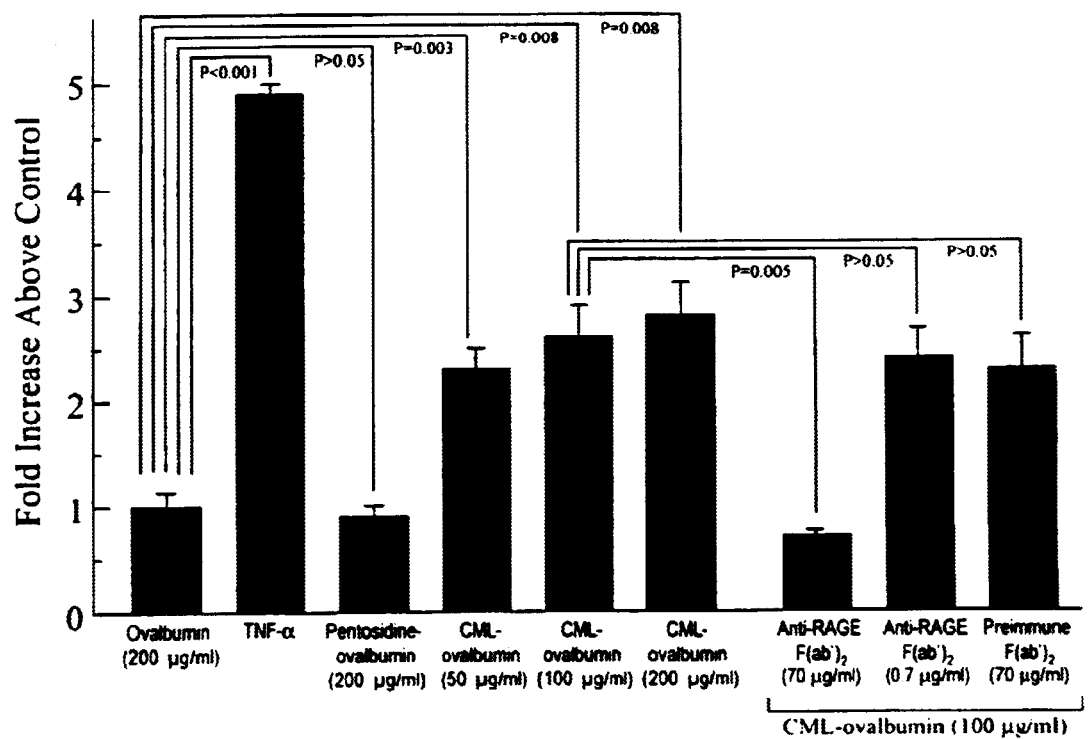
FIG. 4. Cellular activation studies: endothelial cells. HUVEC were incubated in the presence of the indicated mediators for 6 hrs. Where indicated, certain cells were preincubated with anti-RAGE/preimmune IgG for one hour. Cells were washed and incubated with $^{51}$Cr-Molt-4 cells (bear VLA-4) for 1 hr. Bound radioactivity was eluted in the presence of SDS (1%) and counted in a gamma counter. Results are reported compared with Molt-4 cell binding to cells exposed to native ovalbumin (defined as "1").
Figure 5:
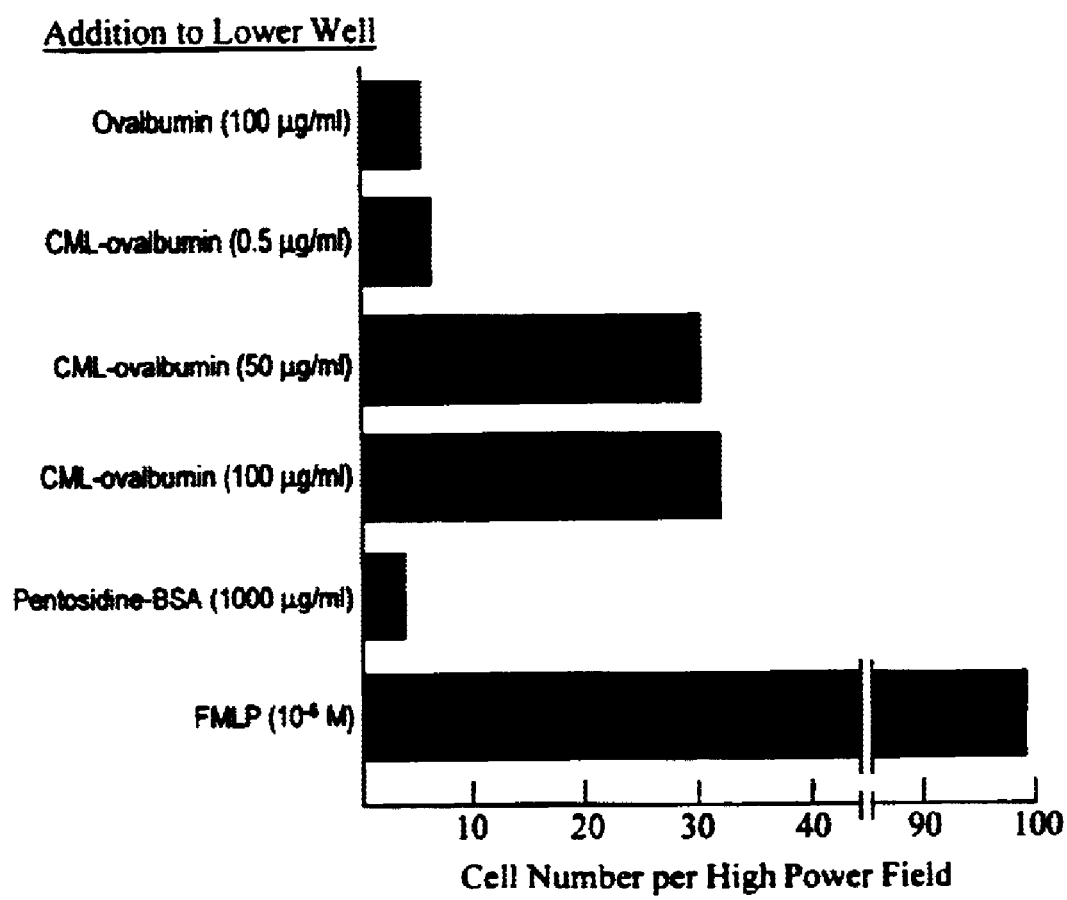
FIG. 5. Cellular activation studies: mononuclear phagocytes. Human monocytes (5×10$^4$) were placed in the upper wells of modified chemotaxis chambers with the indicated mediators in the lower wells for three hrs. Membranes were then stained with Giemsa and cells that migrated through the membrane toward the chemotactic stimulus counted per hpf.

The nucleic acid sequence and amino acid sequence of RAGE has been published in Neeper, M., Schmidt, A. M., Brett, J., Yan, S. D., Wang, F., Pan, Y. C., Elliston, K., Stern, D., and Shaw, A. Cloning and expression of RAGE: a cell surface receptor for advanced glycosylation end products of proteins. J. Biol. Chem. 267:14998–15004, 1992 the contents of which are hereby incorporated by reference. The human cDNA of RAGE is 1406 base pairs and encodes a mature protein of 404 amino acids. See FIG. 3 of Neeper et al. 1992. As used herein, "V-domain of RAGE" refers to the immunoglobulin-like variable domain as shown in FIG. 5 of The V-domain includes amino acids from position 1 to position 120 as shown in FIG. 4 of Neeper et al. (1992). The minimum required amino acid sequence to define the AGE binding site in the RAGE protein may be much smaller than 120 amino acids.

Soluble RAGE (sRAGE) is the RAGE protein free from the cell membrane. For example, sRAGE is not imbedded in the cell surface. In one embodiment, sRAGE comprises the extracellular two-thirds of the amino acid sequence of membrane-bound RAGE.

As used herein "inactivated by derivatization" encompasses a chemical modification of a peptide so as to cause amino groups of the peptide to be less reactive with the chemical modification than without such chemical modification. Examples, of such chemical modification includes making an aryl derivative of the peptide or an alkyl derivative of the peptide. Other derivatives encompass an acetyl derivative, a propyl derivative, an isopropyl derivative, a buytl derivative, an isobutyl derivative, a carboxymethyl derivative, a benzoyl derivative. Other derivatives would be known to one of skill in the art.

In one embodiment of the present invention is a screening assay for identifying a compound capable of inhibiting interaction of a peptide with the AGE binding site of RAGE (e.g., the V-domain or the minimal necessary amino acid sequence required to have binding of an AGE) which comprises: (a) admixing the peptide and a second peptide which has the sequence of the AGE binding site of RAGE and the compound; (b) determining the amount of the peptide bound to the second peptide, and (c) comparing the amount of bound peptide determined in step (b) with the amount determined in the absence of the compound, thus identifying the compound as capable of inhibiting the interaction of the peptide with the AGE binding site of RAGE.

The screening assay may be carried out wherein one of the components is bound or affixed to a solid surface. In one embodiment the peptide is affixed to a solid surface. In another embodiment, the second peptide which has the sequence of the AGE binding site of RAGE is bound or affixed to a solid surface. The solid surfaces useful in this embodiment would be known to one of skill in the art. For example, one embodiment of a solid surface is a bead, a column, a plastic dish, a plastic plate, a microscope slide, a nylon membrane, etc. The material of which the solid surface is comprised is synthetic in one example.

One of the components of step (a) of the screening assay may be detectably labelled. The component (either the compound, the peptide or RAGE or the fragment thereof) may be labeled with a detectable moiety including a fluorescent label, a biotin, a digoxigenin, a radioactive atom, a paramagnetic ion, and a chemiluminescent label. The component in step (a) may be labeled by covalent means such as chemical, enzymatic or other appropriate means with a moiety such as an enzyme or radioisotope.

In one embodiment, the subject is be a mammal. In another embodiment, the subject is a vertebrate. In a preferred embodiment, the mammal is a human. In one example, the subject is a diabetic subject. In another example of the invention, the subject is suffering from diabetes, renal failure, amyloidoses, aging or inflammation. The subject may be an obese subject as defined by the American Medical Association height and weight standards. The subject may be aged. The subject may be a human, a primate, an equine subject, an opine subject, an avian subject, a bovine subject, a porcine, a canine, a feline or a murine subject.

In one embodiment, the subject is suffering from an AGE-related disease. In another embodiment, such AGE-related disease is manifest in the brain, retina, kidney, vasculature, heart, or lung. In another embodiment, the subject is suffering from Alzheimer's disease or a disease which is manifested by AGEs accumulating in the subject. In another embodiment, the subject is suffering from symptoms of diabetes such as soft tissue injury, reduced ability to see, cardiovascular disease, kidney disease, etc. Such symptoms would be known to one of skill in the art.

The compound may be a polypeptide. The polypeptide may be a peptide, a peptidomimetic, a synthetic polypeptide, a derivative of a natural polypeptide, a modified polypeptide, a labelled polypeptide, or a polypeptide which includes non-natural peptides. The peptidomimetic may be identified from screening large libraries of different compounds which are peptidomimetics to determine a compound which is capable of preventing accelerated atherosclerosis in a subject predisposed thereto. The polypeptide may be a non-natural polypeptide which has chirality not found in nature, i.e. D-amino acids or L-amino acids.

In one embodiment, the compound is an antagonist, wherein the antagonist is capable of binding the RAGE with higher affinity than AGEs, thus competing away the effects of AGE's binding.

In another embodiment, the compound is a ribozyme which is capable of inhibiting expression of RAGE. In another embodiment, the compound is an-anti-RAGE antibody, an anti-AGE antibody, an anti-V-domain of RAGE antibody. The antibody may be monoclonal, polyclonal, chimeric, humanized, primatized. The compound may be a fragment of such antibody.

In another embodiment of the present invention, the method may further comprise administering to the subject a pharmaceutically acceptable carrier during the administration of the polypeptide. The administration may comprise intralesional, intraperitoneal, intramuscular or intravenous injection; infusion; liposome-mediated delivery; or topical, nasal, oral, ocular or otic delivery. In a further embodiment, the administration includes intrabronchial administration, anal or intrathecal administration.

The compound may be delivered hourly, daily, weekly, monthly, yearly (e.g. in a time release form) or as a one time delivery. The delivery may be continuous delivery for a period of time, e.g. intravenous delivery.

The effective amount of the compound may comprise from about 0.000001 mg/kg body weight to about 100 mg/kg body weight. In one embodiment, the effective amount may comprise from about 0.001 mg/kg body weight to about 50 mg/kg body weight. In another embodiment, the effective amount may range from about 0.01 mg/kg body weight to about 10 mg/kg body weight. The actual effective amount will be based upon the size of the compound, the biodegradability of the compound, the bioactivity of the compound and the bioavailability of the compound. If the compound does not degrade quickly, is bioavailable and highly active, a smaller amount will be required to be effective. The effective amount will be known to one of skill in the art; it will also be dependent upon the form of the compound, the size of the compound and the bioactivity of the compound. One of skill in the art could routinely perform empirical activity tests for a compound to determine the bioactivity in bioassays and thus determine the effective amount.

In another embodiment of the present invention, the method may further comprise administering a pharmaceutically acceptable carrier to the subject during the administration of the compound. The administration may comprise intralesional, intraperitoneal, intramuscular or intravenous injection; infusion; liposome-mediated delivery; or topical, nasal, oral, ocular or otic delivery.

The compound may be administered hourly, daily, weekly, monthly, yearly (e.g. in a time release form) or as a one time delivery. The delivery or administration may be continuous delivery for a period of time, e.g. intravenous delivery.

The compound may be an sRAGE polypeptide such as a polypeptide analog of sRAGE. Such analogs include fragments of sRAGE. Following the procedures of the published application by Alton et al. (WO 83/04053), one can readily design and manufacture genes coding for microbial expression of polypeptides having primary conformations which differ from that herein specified for in terms of the identity or location of one or more residues (e.g., substitutions, terminal and intermediate additions and deletions). Alternately, modifications of cDNA and genomic genes can be readily accomplished by well-known site-directed mutagenesis techniques and employed to generate analogs and derivatives of sRAGE polypeptide. Such products share at least one of the biological properties of sRAGE but may differ in others. As examples, products of the invention include those which are foreshortened by e.g., deletions; or those which are more stable to hydrolysis (and, therefore, may have more pronounced or longerlasting effects than naturally-occurring); or which have been altered to delete or to add one or more potential sites for O-glycosylation and/or N-glycosylation or which have one or more cysteine residues deleted or replaced by e.g., alanine or serine residues and are potentially more easily isolated in active form from microbial systems; or which have one or more tyrosine residues replaced by phenylalanine and bind more or less readily to target proteins or to receptors on target cells. Also comprehended are polypeptide fragments duplicating only a part of the continuous amino acid sequence or secondary conformations within sRAGE, which fragments may possess one property of sRAGE and not others. It is noteworthy that activity is not necessary for any one or more of the polypeptides of the invention to have therapeutic utility or utility in other contexts, such as in assays of sRAGE antagonism. Competitive antagonists may be quite useful in, for example, cases of overproduction of sRAGE.

Of applicability to peptide analogs of the invention are reports of the immunological property of synthetic peptides which substantially duplicate the amino acid sequence existent in naturally-occurring proteins, glycoproteins and nucleoproteins. More specifically, relatively low molecular weight polypeptides have been shown to participate in immune reactions which are similar in duration and extent to the immune reactions of physiologically-significant proteins such as viral antigens, polypeptide hormones, and the like. Included among the immune reactions of such polypeptides is the provocation of the formation of specific antibodies in immunologically-active animals [Lerner et al., Cell, 23, 309–310 (1981); Ross et al., Nature, 294, 654–658 (1981); Walter et al., Proc. Natl. Acad. Sci. USA, 78, 4882–4886 (1981); Wong et al., Proc. Natl. Sci. USA, 79, 5322–5326 (1982); Baron et al., Cell, 28, 395–404 (1982); Dressman et al., Nature, 295, 185–160 (1982); and Lerner, Scientific American, 248, 66–74 (1983). See also, Kaiser et al. [Science, 223, 249–255 (1984)] relating to biological and immunological properties of synthetic peptides which approximately share secondary structures of peptide hormones but may not share their primary structural conformation.

The compounds of the present invention may be a peptidomimetic compound which may be at least partially unnatural. The peptidomimetic compound may be a small molecule mimic of a portion of the amino acid sequence of sRAGE. The compound may have increased stability, efficacy, potency and bioavailability by virtue of the mimic. Further, the compound may have decreased toxicity. The peptidomimetic compound may have enhanced mucosal intestinal permeability. The compound may be synthetically prepared. The compound of the present invention may include L-, D- or unnatural amino acids, alpha, alpha-disubstituted amino acids, N-alkyl amino acids, lactic acid (an isoelectronic analog of alanine). The peptide backbone of the compound may have at least one bond replaced with PSI-[CH═CH] (Kempf et al. 1991). The compound may further include trifluorotyrosine, p-Cl-phenylalanine, p-Br-phenylalanine, poly-L-propargylglycine, poly-D,L-allyl glycine, or poly-L-allyl glycine.

One embodiment of the present invention is a peptidomimetic compound wherein the compound has a bond, a peptide backbone or an amino acid component replaced with a suitable mimic. Examples of unnatural amino acids which may be suitable amino acid mimics include β-alanine, L-α-amino butyric acid, L-γ-amino butyric acid, L-α-amino isobutyric acid, L-ε-amino caproic acid, 7-amino heptanoic acid, L-aspartic acid, L-glutamic acid, cysteine (acetamindomethyl), N-ε-Boc-N-α-CBZ-L-lysine, N-ε-Boc-N-α-Fmoc-L-lysine, L-methionine sulfone, L-norleucine, L-norvaline, N-α-Boc-N-δCBZ-L-ornithine, N-δ-Boc-N-α-CBZ-L-ornithine, Boc-p-nitro-L-phenylalanine, Boc-hydroxyproline, Boc-L-thioproline. (Blondelle, et al. 1994; Pinilla, et al. 1995).

In one embodiment, the compound is a peptide wherein the free amino groups have been inactivated by derivitization. For example, the peptide may be an aryl derivative, an alkyl derivative or an anhydride derivative. The peptide may be acetylated. The peptide is derivatized so as to neutralize its net charge.

In another embodiment, the compound may be soluble RAGE (sRAGE) or a fragment thereof. Soluble RAGE is not located on the cell surface and is not associated with a cell membrane.

The subject may be a mammal or a non-mammal. The subject may be a human. The subject may be a mouse, a rat, a cow, a monkey, a horse, a pig, or a dog. The subject may be a diabetic subject.

The administration of the compound may be intralesional, intraperitoneal, intramuscular or intravenous injection; infusion; liposome-mediated delivery; topical, nasal, oral, anal, ocular or otic delivery. The administration may be constant for a certain period of time or periodic and at specific intervals. The carrier may be a diluent, an aerosol, a topical carrier, an aqeuous solution, a nonaqueous solution or a solid carrier.

The present invention also provides for a method for inhibiting the interaction of an advanced glycation endproduct (AGE) with a receptor for advanced glycation endproduct (RAGE) in a subject which comprises administering to the subject an amount of quinine or a derivative thereof effective to inhibit the interaction between AGE and RAGE in subject. In one embodiment, the derivative has a different chemical structure than quinine and the derivative has the same overall charge as quinine.

The present invention also provides for a method for inhibiting the interaction of an advanced glycation endproduct (AGE) with a receptor for advanced glycation endproduct (RAGE) in a subject which comprises administering to the subject an amount of quninidine or a derivative thereof effective to inhibit the interaction between AGE and RAGE in subject. In one embodiment, the derivative has a different chemical structure than quinidine and the derivative has the same overall charge as quinidine.

In the practice of any of the methods of the invention or preparation of any of the pharmaceutical compositions a "therapeutically effective amount" is an amount which is capable of preventing interaction of AGE/RAGE in a subject. Accordingly, the effective amount will vary with the subject being treated, as well as the condition to be treated. For the purposes of this invention, the methods of administration are to include, but are not limited to, administration cutaneously, subcutaneously, intravenously, parenterally, orally, topically, or by aerosol.

As used herein, the term "suitable pharmaceutically acceptable carrier" encompasses any of the standard pharmaceutically accepted carriers, such as phosphate buffered saline solution, water, emulsions such as an oil/water emulsion or a triglyceride emulsion, various types of wetting agents, tablets, coated tablets and capsules. An example of an acceptable triglyceride emulsion useful in intravenous and intraperitoneal administration of the compounds is the triglyceride emulsion commercially known as Intralipid®.

Typically such carriers contain excipients such as starch, milk, sugar, certain types of clay, gelatin, stearic acid, talc, vegetable fats or oils, gums, glycols, or other known excipients. Such carriers may also include flavor and color additives or other ingredients.

This invention also provides for pharmaceutical compositions including therapeutically effective amounts of polypeptide compositions and compounds, together with suitable diluents, preservatives, solubilizers, emulsifiers, adjuvants and/or carriers. Such compositions may be liquids or lyophilized or otherwise dried formulations and include diluents of various buffer content (e.g., Tris-HCl., acetate, phosphate), pH and ionic strength, additives such as albumin or gelatin to prevent absorption to surfaces, detergents (e.g., Tween 20, Tween 80, Pluronic F68, bile acid salts), solubilizing agents (e.g., glycerol, polyethylene glycerol), anti-oxidants (e.g., ascorbic acid, sodium metabisulfite), preservatives (e.g., Thimerosal, benzyl alcohol, parabens), bulking substances or tonicity modifiers (e.g., lactose, mannitol), covalent attachment of polymers such as polyethylene glycol to the compound, complexation with metal ions, or incorporation of the compound into or onto particulate preparations of polymeric compounds such as polylactic acid, polglycolic acid, hydrogels, etc, or onto liposomes, micro emulsions, micelles, unilamellar or multi lamellar vesicles, erythrocyte ghosts, or spheroplasts. Such compositions will influence the physical state, solubility, stability, rate of in vivo release, and rate of in vivo clearance of the compound or composition. The choice of compositions will depend on the physical and chemical properties of the compound.

Controlled or sustained release compositions include formulation in lipophilic depots (e.g., fatty acids, waxes, oils). Also comprehended by the invention are particulate compositions coated with polymers (e.g., poloxamers or poloxamines) and the compound coupled to antibodies directed against tissue-specific receptors, ligands or antigens or coupled to ligands of tissue-specific receptors. Other embodiments of the compositions of the invention incorporate particulate forms protective coatings, protease inhibitors or permeation enhancers for various routes of administration, including parenteral, pulmonary, nasal and oral.

When administered, compounds are often cleared rapidly from the circulation and may therefore elicit relatively short-lived pharmacological activity. Consequently, frequent injections of relatively large doses of bioactive compounds may by required to sustain therapeutic efficacy. Compounds modified by the covalent attachment of water-soluble polymers such as polyethylene glycol, copolymers of polyethylene glycol and polypropylene glycol, carboxymethyl cellulose, dextran, polyvinyl alcohol, polyvinylpyrrolidone or polyproline are known to exhibit substantially longer half-lives in blood following intravenous injection than do the corresponding unmodified compounds (Abuchowski et al., 1981; Newmark et al., 1982; and Katre et al., 1987). Such modifications may also increase the compound's solubility in aqueous solution, eliminate aggregation, enhance the physical and chemical stability of the compound, and greatly reduce the immunogenicity and reactivity of the compound. As a result, the desired in vivo biological activity may be achieved by the administration of such polymer-compound adducts less frequently or in lower doses than with the unmodified compound.

Attachment of polyethylene glycol (PEG) to compounds is particularly useful because PEG has very low toxicity in mammals (Carpenter et al., 1971). For example, a PEG adduct of adenosine deaminase was approved in the United States for use in humans for the treatment of severe combined immunodeficiency syndrome. A second advantage afforded by the conjugation of PEG is that of effectively reducing the immunogenicity and antigenicity of heterologous compounds. For example, a PEG adduct of a human protein might be useful for the treatment of disease in other mammalian species without the risk of triggering a severe immune response. The polypeptide or composition of the present invention may be delivered in a microencapsulation device so as to reduce or prevent an host immune response against the polypeptide or against cells which may produce the polypeptide. The polypeptide or composition of the present invention may also be delivered microencapsulated in a membrane, such as a liposome.

Polymers such as PEG may be conveniently attached to one or more reactive amino acid residues in a protein such as the alpha-amino group of the amino terminal amino acid, the epsilon amino groups of lysine side chains, the sulfhydryl groups of cysteine side chains, the carboxyl groups of aspartyl and glutamyl side chains, the alpha-carboxyl group of the carboxy-terminal amino acid, tyrosine side chains, or to activated derivatives of glycosyl chains attached to certain asparagine, serine or threonine residues.

Numerous activated forms of PEG suitable for direct reaction with proteins have been described. Useful PEG reagents for reaction with protein amino groups include active esters of carboxylic acid or carbonate derivatives, particularly those in which the leaving groups are N-hydroxysuccinimide, p-nitrophenol, imidazole or 1-hydroxy-2-nitrobenzene-4-sulfonate. PEG derivatives containing maleimido or haloacetyl groups are useful reagents for the modification of protein free sulfhydryl groups. Likewise, PEG reagents containing amino hydrazine or hydrazide groups are useful for reaction with aldehydes generated by periodate oxidation of carbohydrate groups in proteins.

Pharmaceutical with Carriers

In one preferred embodiment the pharmaceutical carrier may be a liquid and the pharmaceutical composition would be in the form of a solution. In another equally preferred embodiment, the pharmaceutically acceptable carrier is a solid and the composition is in the form of a powder or tablet. In a further embodiment, the pharmaceutical carrier is a gel and the composition is in the form of a suppository or cream. In a further embodiment the active ingredient may be formulated as a part of a pharmaceutically acceptable transdermal patch.

A solid carrier can include one or more substances which may also act as flavoring agents, lubricants, solubilizers, suspending agents, fillers, glidants, compression aids, binders or tablet-disintegrating agents; it can also be an encapsulating material. In powders, the carrier is a finely divided solid which is in admixture with the finely divided active ingredient. In tablets, the active ingredient is mixed with a carrier having the necessary compression properties in suitable proportions and compacted in the shape and size desired. The powders and tablets preferably contain up to 99% of the active ingredient. Suitable solid carriers include, for example, calcium phosphate, magnesium stearate, talc, sugars, lactose, dextrin, starch, gelatin, cellulose, polyvinylpyrrolidine, low melting waxes and ion exchange resins.

Liquid carriers are used in preparing solutions, suspensions, emulsions, syrups, elixirs and pressurized compositions. The active ingredient can be dissolved or suspended in a pharmaceutically acceptable liquid carrier such as water, an organic solvent, a mixture of both or pharmaceutically acceptable oils or fats. The liquid carrier can contain other suitable pharmaceutical additives such as solubilizers, emulsifiers, buffers, preservatives, sweeteners, flavoring agents, suspending agents, thickening agents, colors, viscosity regulators, stabilizers or osmo-regulators. Suitable examples of liquid carriers for oral and parenteral administration include water (partially containing additives as above, e.g. cellulose derivatives, preferably sodium carboxymethyl cellulose solution), alcohols (including monohydric alcohols and polyhydric alcohols, e.g. glycols) and their derivatives, and oils (e.g. fractionated coconut oil and arachis oil). For parenteral administration, the carrier can also be an oily ester such as ethyl oleate and isopropyl myristate. Sterile liquid carriers are useful in sterile liquid form compositions for parenteral administration. The liquid carrier for pressurized compositions can be halogenated hydrocarbon or other pharmaceutically acceptable propellent.

Liquid pharmaceutical compositions which are sterile solutions or suspensions can be utilized by for example, intramuscular, intrathecal, epidural, intraperitoneal or subcutaneous injection. Sterile solutions can also be administered intravenously. The active ingredient may be prepared as a sterile solid composition which may be dissolved or suspended at the time of administration using sterile water, saline, or other appropriate sterile injectable medium. Carriers are intended to include necessary and inert binders, suspending agents, lubricants, flavorants, sweeteners, preservatives, dyes, and coatings.

The active ingredient of the present invention (i.e., the compound identified by the screening method or composition thereof) can be administered orally in the form of a sterile solution or suspension containing other solutes or suspending agents, for example, enough saline or glucose to make the solution isotonic, bile salts, acacia, gelatin, sorbitan monoleate, polysorbate 80 (oleate esters of sorbitol and its anhydrides copolymerized with ethylene oxide) and the like.

The active ingredient can also be administered orally either in liquid or solid composition form. Compositions suitable for oral administration include solid forms, such as pills, capsules, granules, tablets, and powders, and liquid forms, such as solutions, syrups, elixirs, and suspensions. Forms useful for parenteral administration include sterile solutions, emulsions, and suspensions.

In another embodiment of the present invention, the subject may have diabetes. The subject may demonstrate complications associated with diabetes. Some examples of such complications include activation of endothelial and macrophage AGE receptors, altered lipoproteins, matrix, and basement membrane proteins; altered contractility and hormone responsiveness of vascular smooth muscle; altered endothelial cell permeability; sorbitol accumulation; neural myoinositol depletion or altered Na—K ATPase activity. Such complications are discussed in a recent publication by Porte and Schwartz, Diabetes Complications: Why is Glucose potentially Toxic?, Science, Vol. 272, pages 699–700.

This invention is illustrated in the Experimental Details section which follows. These sections are set forth to aid in an understanding of the invention but are not intended to, and should not be construed to, limit in any way the invention as set forth in the claims which follow thereafter.

EXPERIMENTAL DETAILS

EXAMPLE 1

Carboxymethyl-lysine Adducts of Proteins (CML) are Advanced Glycation Endproducts (AGEs) that Ligate the Receptor for AGE (RAGE) to Activate Cell Signalling Pathways and Modulate Gene Expression In Vitro and In Vivo Advanced Glycation Endproducts (AGEs), the modified class of compounds that result from the processes of glycoxidation, are an heterogeneous class of structures whose accumulation in the plasma and tissues has been linked to a range of complications that occur in disorders such as aging, diabetes, renal failure and inflammation. AGEs impart pathogenic effects in a number of ways; in one of these, ligation of cell surface receptors such as RAGE triggers multiple mechanisms that result in cellular perturbation and dysfunction. In order to determine which one(s) of known AGE structures interact with RAGE, we prepared a series of synthetic AGEs and tested their ability to interact with RAGE. CML-modified BSA (not free CML), but not pentosidine or methylglyoxal-modified forms of proteins, bound RAGE in a dose-dependent manner, with $K_d \approx 76 \pm 3.7$ nM. Competition studies identified the V-domain of RAGE as the Ig-type domain containing interaction sites for CML modifications. In cell culture studies, CML-modified forms of proteins increased cell surface VCAM-1 functional activity on human umbilical vein endothelial cells (HUVECs) and increased migration of human peripheral blood-derived mononuclear phagocytes (MPs) in a RAGE-dependent manner. In addition, incubation of HUVEC with CML-modified protein, but not pentosidine-modifications, resulted in activation of NF-κB, a process inhibited in the presence of anti-RAGE IgG, excess soluble RAGE or transfection with a construct encoding cytosolic tail-deleted RAGE (a dominant negative effect). Infusion of CML-modified BSA, but not native protein, into normal mice increased mRNA for VCAM-1 in the lung. Both CML- and RAGE epitopes were increased and co-localized in the kidney tissue from human subjects with diabetes or systemic lupus erythematosus, consistent with a role for their interaction in the cellular perturbation characteristic of these disorders. Our studies identify CML-modified structures and V-domain of RAGE as a critical target for the design of agents to block the development of cellular perturbation, and, perhaps, the complications of the vasculature and inflammatory cells that characterize disorders of AGE (CML) accumulation.

To date, a number of important AGE structures have been identified, characterized and localized to the tissues. However, it is not clear which products of glycoxidation mediate receptor-independent and receptor-dependent effects. $N^\epsilon$-(Carboxymethyl)lysine (CML), a product of both lipid peroxidation and glycoxidation, has been reported to be a predominant AGE in aging and diabetes (24–27). Schleicher and colleagues (25) demonstrated increased CML content in the serum of patients with diabetes. Furthermore, CML content increased in skin, lung, heart, liver, kidney, intestine, intervertebral discs and particularly in arteries with aging; a process accelerated in diabetes. High levels of CML modification were also observed in atherosclerotic plaques and foam cells. Pentosidine, also a product of glycoxidation, forms as a cross-link between lysine and arginine and may result from glycoxidation of Amadori products or the reaction of arabinose, an autoxidative product of glucose (27). Accumulation of pentosidine has been demonstrated in diabetic and aged tissues (27–28). Pyrraline, a glycation product resulting from the interaction of proteins with 3-deoxyglucosone, structures that eventuate from the generation of Amadori products, has been recently identified in diabetic kidney (27,29). Evidence has been presented that methylglyoxal AGE-modifications exist in vivo. Methylglyoxal (MG) compounds are major intermediates in the Maillard reaction and may be formed in a number of metabolic pathways, including glycation and sugar autoxidation (30). Nagaraj and colleagues demonstrated increased MG immunoreactivity in the serum of diabetic patients compared with controls, as well as in the stromal region of cornea from aged subjects (30). Indeed, it has recently been shown that MG-modifications of proteins may interact with macrophages-like cells in culture to induce production of cytokines such as interleukin-1β, although underlying molecular mechanisms have yet to be identified.

A number of common AGE structures, such as CML-, pentosidine, and methylglyoxal modifications of proteins have been prepared and it is first reported herein that CML-modifications of proteins, at least in part, are ligands for RAGE. Furthermore, consistent with our previous observations, CML-modifications of proteins interact with the V-type immunoglobulin domain of RAGE (31).

These data provide a framework for the development of screening strategies to identify structures to inhibit the interaction of pathologic AGEs such as CML-modifications with RAGE. Such structures are likely to form the basis for therapeutic intervention in a range of disorders in which AGEs such as CML form, including, but not limited to, diabetes, renal failure, amyloidoses, aging, Alzheimer's Disease and inflammation.

MATERIALS AND METHODS

Radioligand binding assays. CML (free), CML-modifications of proteins, pentosidine (free), pentosidine modifications of proteins, methylglyoxal modifications of proteins were prepared according to previously published methods (24–30). All materials were devoid of endotoxin using the Detoxi-gel system (PIERCE®) and tested for negativity in the limulus amebocyte assay (SIGMA®). Gas chromatography-mass spectroscopy and HPLC analyses were performed and verified the identity of the prepared AGES. Specific AGE or control protein (5 μg) was loaded onto the wells of a NUNC MAXISORP® dish in sodium bicarbonate/sodium carbonate buffer (pH 9.8) overnight at 4° C. The following morning, wells were aspirated and blocked with phosphate buffered saline (with calcium/magnesium) containing bovine serum albumin (1%) for two hrs at 37° C. Wells were then washed once with phosphate buffered saline (without calcium/magnesium) containing Tween 20 (0.05%); 0.150 ml/well. A radioligand binding assay was then performed in phosphate buffered saline containing 0.2% bovine serum albumin for 2 hrs at 37° C.

utilizing radiolabelled ($^{125}$I; using Iodogen (Pierce)) full length soluble RAGE (100 nM; specific activity 7,000–8,000 cpm/ng) in the presence or absence of unlabelled soluble RAGE (50×molar excess) or the indicated molar excess of competitor. Wells were then eluted after washing as above with buffer containing NP-40 (1%) and NaCl (0.15M). The material retrieved was then counted in a gamma counter (LKB). In certain experiments, antibodies or excess soluble RAGE were employed as indicated to test their ability to compete in the indicated assays.

Constructs. The GST-fusion protein system was utilized to prepared soluble V-domain, and soluble C1 and C2-domains according to the manufacturer's instructions (PHARMACIA®)

Molt-4 binding assays. Molt-4 binding assays were performed according to the general method of Marui et al (32). Human umbilical vein endothelial cells were stimulated with the indicated compound in the presence or absence of competitors for 6 hrs at 37° C. Molt-4 cells, which express VLA-4, ligand for VCAM-1, (ATCC) were grown in RPMI 1640 containing fetal bovine serum (10%). Radio labelling was accomplished by incubating Molt-4 cells (2×10$^7$ cells/ml) for 16 hrs at 37° C. in the above medium containing $^{51}$-Cr (0.2 mCi/ml). Before the binding assay, unincorporated radioactivity was removed by washing cells with Hank's balanced salt solution, and then resuspending them in RPMI containing fetal bovine serum (10%) at 4×10$^6$ cells/ml. Molt-4 cells were incubated with endothelial cells for one hr at 37° C., and nonadherent cells were removed by washing twice with Medium 199 containing fetal bovine serum (1%); adherent cells were solubilized in SDS (1%), and radioactivity counted in a gamma counter.

Chenotaxis assays. Chemotaxis assays, performed in 48-well microchemotaxis chambers (Neuro-Probe) containing polycarbonate membranes were performed as previously described (15). In these studies, human peripheral blood-derived mononuclear phagocytes, which bear cell surface RAGE, were employed.

Electrophoretic mobility shift assays (EMSA). Nuclear extracts were prepared from HUVECs by the method of Schreiber (33). Protein concentration was determined using the Bradford reagent (BIO-RAD®). Double-stranded oligonucleotides representing a portion of the human VCAM-1 promoter containing an NF-κB site were synthesized (Life Technologies). Oligonucleotides were used as probe as follows: NF-κB: 5'CCTTGAAGGGATTTCCCTCC3' (SEQ ID No. 1). Probes were 5'-end labelled with g-[$^{32}$P] ATP and polynucleotide kinase. Each reaction contained 10 fmol of probe and 2–5 microliter (1.5 μg) of nuclear extract. Binding reactions were performed in buffer as previously described (19). Complexes were resolved on nondenaturing polyacrylamide gels (6%) in tris (50 mM), borate (45 mM), and EDTA (0.5 mM), (0.5×TE buffer; final pH 7.5). Samples were subjected to electrophoresis for 2 hrs at 10 V/cm. For supershift assays, complexes were preincubated with anti-p65 IgG, anti-p50 IgG or both together, or nonimmune IgG (7.5 μg/ml; 2 hrs 37° C.) in a total reaction volume of 20 μl.

Northern blot analysis. Northern blot analysis for VCAM-1 and G3PDH were performed as previously described (19).

Immunohistochemistry. Affinity-purified anti-CML and anti-pentosidine IgG were prepared after incubation of the indicated AGE/Keyhole limpet hemocyanin into rabbits. The IgG was then purified on Protein A columns (PIERCE®) and antibodies solely directed against unmodified KLH were removed by chromatography onto an affigel column (Bio-Rad) to which had been adsorbed KLH (SIGMA®). The material that did not adhere to the column was then chromatographed onto an affigel column to which had been adsorbed the indicated AGE-BSA. Material was then eluted with NaCl (1M) and tested for specificity by ELISA. Immunohistochemistry for RAGE was performed using monospecific polyclonal anti-RAGE IgG. All antibodies were prepared in rabbits and immunohistochemistry performed as previously described on formalin-fixed, paraffin-embedded tissue (10,14,17,20).

RESULTS

Figure 2:
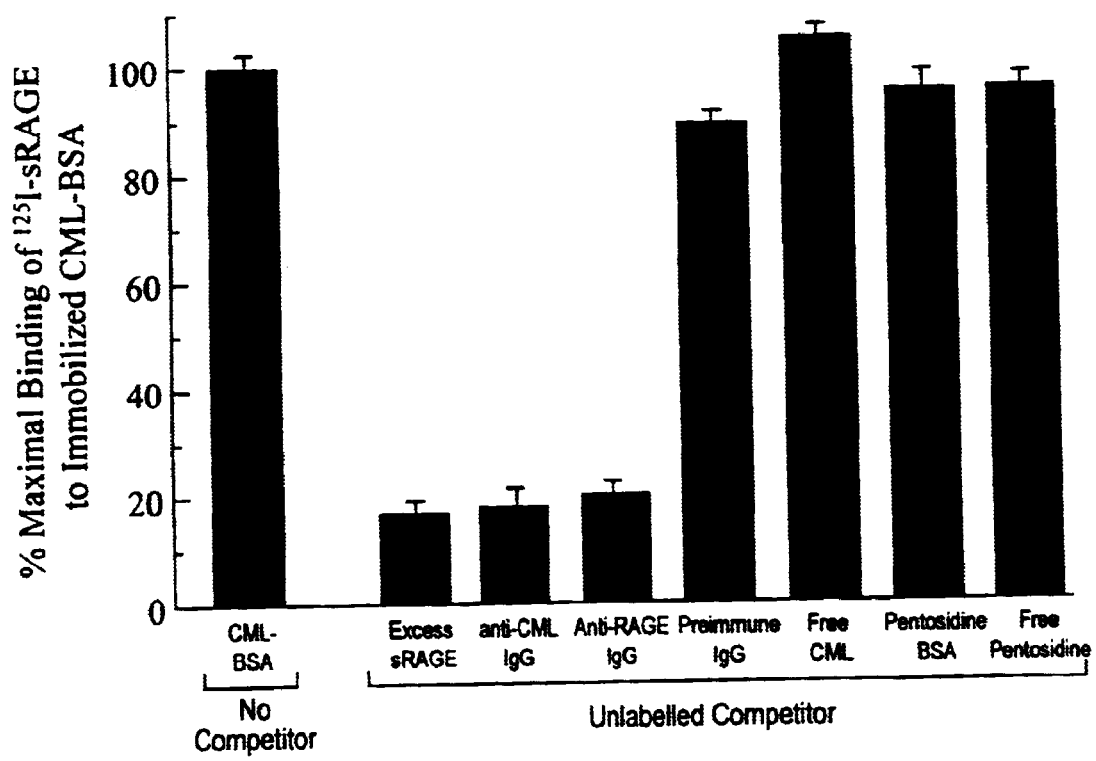
FIG. 2. Radioligand binding studies: competition experiments. CML-BSA was immobilized to wells; binding was performed with $^{125}$-I sRAGE (100 nM) with the indicated competitors. Excess sRAGE, anti-CML IgG and anti-RAGE IgG inhibited binding of sRAGE to CML-BSA. Percent maximal binding is reported compared to binding to immobilized CML-BSA without competitor (100%).

Radioligand binding studies. We prepared synthetic specific AGEs as described above. Gas chromatography-mass spectroscopy and HPLC analyses were performed and verified CML- and pentosidine-modifications of proteins. Radioligand binding assays were performed in which CML-BSA, pentosidine-BSA or methylglyoxal-human serum albumin was adsorbed to plastic wells. Radioligand binding assays were performed as described and equilibrium binding data was analyzed according to the equation of Klotz and Hunston. Only CML-BSA (closed circles) bound sRAGE in a dose-dependent manner with $K_D \approx 76 \pm 3.7$ nM (similar to that observed with heterogeneous AGE binding to RAGE, 50–75 nM (4, 15). In contrast, pentosidine-BSA exhibited no specific binding to sRAGE (open circles) (FIG. 1). Furthermore, methylglyoxal-HSA also did not bind specifically to RAGE. That the binding of CML-modifications to RAGE was specific and required modification of peptide by CML was indicated by experiments in which incubation with anti-CML IgG or anti-RAGE IgG significantly reduced binding of CML-BSA to RAGE. In contrast, preimmune IgG, free CML or free pentosidine had no effect (FIG. 2). Binding of CML-BSA to RAGE occurred via interaction with the V-type Ig domain of RAGE, and not by interaction with either the first or second C-type Ig domains of RAGE (FIG. 3).

Cellular Activation Studies.

Endothelial cells, Engagement of cell surface RAGE by mixtures of AGEs prepared by in vitro glycoxidation or patient-derived AGEs induces cellular activation. To test if incubation of CML-ovalbumin or pentosidine-ovalbumin activated EC, specific AGEs were rendered free of endotoxin (Detoxigel columns (PIERCE®)) and tested for absence of endotoxin by limulus amebocyte assay (SIGMA®). Exposure of cultured HUVEC to CML-ovalbumin resulted in a significant 2.3-fold increase in binding of radiolabelled $^{51}$Cr-Molt 4 cells (which bear counterligand to VCAM-1, VLA-4; ref 24) to HUVEC, a process inhibited by anti-RAGE F(ab')$_2$ (dose-dependent) but not by preimmune F(ab')$_2$. In contrast, native ovalbumin and pentosidine-ovalbumin were without effect (FIG. 4). Furthermore, incubation of CML-ovalbumin with excess sRAGE also diminished binding of Molt-4 cells to HUVEC (value was identical to that observed with incubation of cells with unmodified ovalbumin). These data suggest that incubation of HUVEC with CML-ovalbumin results in increased cell surface VCAM-1.

Mononuclear phagocytes. To determine if CML-ovalbumin mediated increased human peripheral blood-derived monocyte chemotaxis, experiments were performed in modified chemotaxis chambers as described above. When placed in the lower wells of chemotaxis chambers, CML-ovalbumin stimulated monocyte chemotaxis in a dose-dependent manner. In contrast, native ovalbumin or pentosidine BSA were without effect (FIG. 5). Furthermore, in the presence of anti-RAGE F(ab')$_2$ or excess sRAGE, CML ovalbumin-mediated monocyte chemotaxis was completely inhibited.

Figure 6:
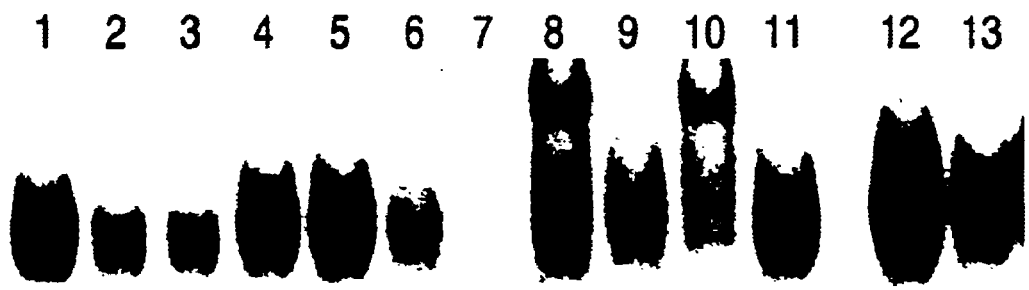
FIG. 6. Electrophoretic mobility shift assay. Human umbilical vein endothelial cells (HUVEC) were incubated with mediators for 6 hrs; nuclear extracts were prepared and electrophoretic mobility shift assays performed with $^{32}$P-labelled probe for NF-κB. Lanes contain mediators as above (all AGEs were added at 50 µg/ml). Lanes contain: lane 1, CML-ovalbumin; lane 2, native ovalbumin; lane 3, pentosidine ovalbumin; lane 4, nonimmune IgG and CML ovalbumin; lane 5, anti-RAGE IgG: 7 µg/ml; lane 6; anti-RAGE IgG: 70 µg/ml; lane 7: CML-ovalbumin/100-fold excess unlabelled NF-κB. Supershift assays (lane 8: anti-p50 IgG; lane 9:anti-p65 IgG; lane 10:both anti-p50 IgG and anti-p65 IgG; lane 11: preimmune IgG), all + CML-ovalbumin. Lane 12:CML-ovalbumin: vector alone/13:tail-deleted RAGE.

CML-ovalbumin-RAGE interaction activates NF-κB in HUVEC. These data suggested that interaction of CML-modified proteins with EC and MP RAGE activates specific cell signalling pathways. We previously demonstrated that ligation of RAGE by heterogeneous AGEs results in enhanced cellular oxidant stress, a process largely mediated by activation of NADPH oxidase (14,20), with increased activity of p21$^{ras}$ and erk 1/erk 2 kinases as oxidant-sensitive proximal events involved in activation of NF-κB (20). We tested the ability of CML-ovalbumin to ligate RAGE and activate cell signalling pathways. Incubation of HUVEC with CML-ovalbumin, but not native ovalbumin or pentosidine ovalbumin resulted in increased nuclear translocation of NF-κB (FIG. 6, lanes 1, 2 and 3, respectively). That this was due to interaction of CML-ovalbumin with cellular RAGE was demonstrated by experiments in which pretreatment of HUVEC with high, but not low concentrations of anti-RAGE IgG inhibited activation of NF-κB (FIG. 6, lanes 6 and 5, respectively). Pretreatment with preimmune IgG was without effect (FIG. 6, lane 4). Incubation of CML-ovalbumin with excess sRAGE also inhibited activation of NF-B. The nuclear complex induced by ligation of RAGE by CML-ovalbumin was a heterodimer of p50/p65 NF-κB in supershift assays (FIG. 6, lanes 8–11). The central role of RAGE in these CML-ovalbumin-mediated phenomena was further delineated in experiments in which HUVEC were transiently transfected with a construct encoding RAGE lacking the cytosolic domain. Upon transient transfection into HUVEC CML-ovalbumin mediated activation of NF-κB was significantly diminished; transfection with vector alone was without effect (FIG. 6, lanes 13 and 12, respectively).

Figure 7:
FIG. 7. In vivo studies: infusion of CML-BSA into mice modulates gone expression. CML-BSA (lane 2) or native BSA (lane 1) (both 100 µg) was infused into normal CD1 mice. LPS (100 μg) was infused as positive control (lane 3). Six hrs later, mice were humanely sacrificed and lungs rapidly removed for preparation of RNA. Northern analysis was performed as described above for VCAM-1; membranes were then stripped and reprobed with $^{32}$-P-labelled cDNA for G3PDH.
Figure 7:
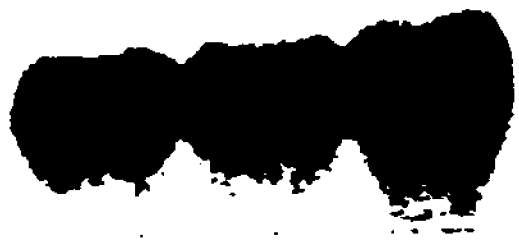

Infusion of CML-BSA into normal mice increases mRNA for Vascular Cell Adhesion Molecule-1. Consistent with an important role for CML-modified forms of proteins in modulating gene expression in vivo, infusion of CML-BSA into CD-1 mice resulted in increased mRNA for VCAM-1 in lung tissue by Northern blot analysis (FIG. 7, lane 2). In contrast, infusion of unmodified BSA was without effect (FIG. 7, lane 1).

Identification of CML and pentosidine epitopes in human diabetic kidney. In our previous studies using affinity-purified IgG to heterogeneous AGEs, we demonstrated strikingly increased and co-localized expression of AGEs with vascular RAGE in diabetic kidney (13). We thus prepared affinity-purified anti-CML and anti-pentosidine IgG using these AGE modified forms of KLH (keyhole limpet hemocyanin; a potent immunogen) (25). Using these antibodies, we have identified in kidney tissue from a human subject with diabetic nephropathy increased immunoreactivity for pentosidine and CML (FIGS. 8A and 8B, respectively). RAGE expression was markedly upregulated, especially in podocytes (FIG. 8C) and vascular ECs and SMCs and co-localized with increased expression of CML-modifications. Staining for pentosidine, CML and RAGE in age-matched kidney was nearly negative. Taken together, these data further suggest that an important relationship may exist between CML-modified AGEs and cellular RAGE in vivo.

CML and RAGE are Increased in Inflamatory Lupus Nephritis. In unpublished observations from our laboratory, high levels of RAGE expression were noted in vascular tissue from human subjects with temporal arteritis and systemic lupus erythematosus (SLE). We recently reported that RAGE expression in ECs and VSMCs is increased by treatment with LPS (34). Examination of the promoter for RAGE revealed two functional NF-κB binding sites; simultaneous mutation of these resulted in abrogation of enhanced RAGE expression by inflammatory stimuli. Together with recent information linking formation of CML to inflammatory processes (by the myeloperoxidase pathway) (3), we hypothesized that RAGE might play a role in mediating cellular perturbation by inflammatory stimuli. Consistent with this hypothesis, in kidney tissue from a human subject with active lupus nephritis, increased immunoreactivity for CML was noted (FIG. 9a), along with increased and co-localized expression of RAGE, especially within the podocytes (FIG. 9b) and vasculature.

DISCUSSION

As would be expected, a wide range of AGEs may form and accumulate in vivo. However, the precise biologic relevance of each specific AGE has yet to be identified. We previously demonstrated that AGEs prepared in vitro, by incubation of proteins with aldose sugars such as glucose, glucose-6-phosphate or ribose, a heterogeneous mixture (or in vivo derived AGEs using anti-AGE IgGs as the screening agent), contained structure(s) capable of ligating the Receptor for AGE (RAGE) in a manner linked to activation of cell signalling pathways and modulation of gene expression. In the present work, we have extended our findings to show that the most predominant AGE in diabetes and aging (24–25), carboxymethyl-lysine adducts of proteins, is capable of interacting with RAGE (V-type Ig domain) to initiate cell signalling and altered gene expression. In contrast, another AGE, pentosidine, does not bind to nor activate cells in a manner linked to perturbation and dysfunction.

It must be noted that at this time, however, that our findings do not exclude other AGEs as ligands for RAGE. Commonly studied AGEs such as pentosidine- and methylglyoxal adducts, however, have largely been eliminated from consideration. Nevertheless, studies are underway at this time to synthesize, characterize and test other AGEs in this context.

In conclusion, our present findings represent a critical leap in understanding important AGEs that may form/accumulate in vivo capable of activating cells leading to pathways likely linked to vascular and inflammatory cell perturbation. These data importantly extend our knowledge regarding pathogenic AGEs likely involved in the development of complications that arise in a range of AGE (CML-) associated disorders such as diabetes, aging, inflammation and renal failure by providing a targetted, directed framework for the development of strategies designed to discover agents capable of blocking the interaction of pathogenic AGE (CML-adducts) with their cellular receptor RAGE.

A screening assay was performed which identified quinine and quinidine as two compounds each capable of inhibiting the interaction between AGE and RAGE. The assay was performed as follows: CML-modified AGE-BSA was affixed to a plastic dish in an appropriate binding solution. Radiolabelled V-domain of RAGE was admixed to the solution with either unlabelled quinine or qunidine. The results of the assay showed that both qunine and quinidine were able to decrease the binding of the V-domain of RAGE to AGE. The present invention provides for a method for inhibiting the interaction of an advanced glycation endproduct with a recepotr for advanced glycation endproducts in a subject which comprises administering quinine or a derivative thereof or quinidine or a derivative thereof in an amount effective to inhibit the interaction of AGE with RAGE in the subject. For example, a derivative of quinine may be prepared by chemical modification of quinine which chemical modification alters the structure of quinine but does not alter the charge of the quinine molecule. For example, the charge distribution over the molecule will remain the same, however, the chemical structure itself may be altered. In addition, a derivative of quinidine may be prepared similarly as above described for quinine. Again, the charge of the quinidine molecule would not change following the chemical modification, however the chemical structure of the molecule may be altered.

EXAMPLE 2

Carboxymethyl-lysine (CML) Advanced Glycation Endproduct (AGE) Modifications of Ligand for RAGE that Activate Cell Signalling Pathways Advanced glycation endproducts (AGEs) are heterogeneous compounds that form in hyperglycemia, highly-oxidized environments and renal failure. AGEs accumulate in the plasma and tissues of patients with diabetes; their presence has been linked to the development of medical complications. Interaction of AGEs with Receptor for AGE (TAGE) activates cells such as endothelial cells (Ecs) and monocytes (Mps) in a manner favoring the development of vascular/inflammatory cell complications. AGEs consist of structures such as carboxymethyl-lysine and pentosidine (both free and protein-bound forms). To begin to delineate which AGE forms interact with RAGE, we prepared free CML and pentosidine, as well as CML- and pentosidine bovine serum albumin (BSA) and ovalbumin (OVA). CML-BSA and CML-OVA bound immobilized RAGE in a dose-dependent and saturable manner, with Kd=60 nM, a process inhibited in the presence of anti-RAGE IgG and soluble RAGE (sRAGE), but not by nonimmune IgG, BSA, OVA, free CML or free pentosidine. Exposure of Ecs to CML-OVA activated NF-κB and increased binding of Molt-4 cells (which bear the counter-ligand for VCAM-1, VLA-4); processes blocked in the presence of anti-RAGE IgG. In contrast, pentosidine-BSA was without effect. Furthermore, exposure of MPs to CML-BSA or CML-OVA activated NF-κB in a RAGE dependent manner. Pentosidine BSA was without effect. These data identify CML modifications of proteins as ligands of RAGE that activate cell signalling pathways and alter gene expression. Taken together, these data provide an improved understanding of pathogenic AGEs in disorders such as diabetes, and provide a framework for identification of targetted inhibitors.

REFERENCES

1. Brownlee, M. A., Cerami, A., and Vlassara, H. Advanced glycosylation end products in tissue and the biochemical basis of diabetic complications. N. Engl. J. Med. 318:1315–1321, 1988.
2. Dyer, D. G. Dunn, J. A., Thorpe, S. R., Bailie, K. E., Lyons, T. J., McCance, D. R., and Baynes, J. W. Accumulation of Maillard reaction products in skin collagen in diabetes and aging. J. Clin. Invest. 91:2463–2469, 1993.
3. Anderson, M. M, Requena, J. R., Thorpe, S. R., and Heinecke, J. W. A novel mechanism for the generation of Advanced Glycation Endproducts by activated phagocytes at sites of inflammation. Circulation (Supplement) 96:#2331, I-417, 1997.
4. Schmidt, A-M, Vianna, M, Gerlach, M, Brett, J, Ryan, J, Kao, J, Esposito, C, Hegarty, H, Hurley, W, Clauss, M, Wang, F, Pan, Y-C, Tsang, T, and Stern D. Isolation and characterization of binding proteins for advanced glycation endproducts from lung tissue which are present on the endothelial cell surface. J. Biol. Chem. 267:14987–14997, 1992.
5. Schmidt, A-M, Mora, R, Cao, R, Yan, S-D, Brett, J, Ramarkrishnan, R, Tsang, T-C, Simionescu, M, and Stern D. The endothelial cell binding site for advanced glycation endproducts consists of a complex: an integral membrane protein and a lactoferrin-like polypeptide. J. Biol. Chem. 269:9882–9888, 1994.
6. Schmidt, A-M, Hori, O, Brett, J, Yan, S-D, Wautier, J-L, and Stern D. Cellular receptors for advanced glycation end products. Arterioscler. Thromb. 14:1521–1528, 1994.
7. Vlassara, H, Li, Y M, Imani, F, Wojciechowicz, D, Yang, Z, Liu, F T, and Cerami, A. Identification of Galectin-2 as a high affinity binding protein for Advanced Glycation Endproducts (AGE): a new member of the AGE-Receptor complex. Molecular Medicine 1:634–646, 1995.
8. Yang, Z, Makita, J, Horii, Y, Brunelle, S, Cerami, A, Sehajpal, P, Suthanthiran, M, and Vlassara, H. Two novel rat liver membrane proteins that bind AGEs: relation to macrophage receptor for glucose-modified proteins. J. Exp. Med. 174:515–524, 1991.
9. Khoury, J. Thomas, C, Loike, J, Hickman, S, Cao, L, Silverstein, S. Macrophages adhere to glucose-modified basement membrane via their scavenger receptors. J. Biol. Chem. 269:10197–10200, 1994.
10. Brett, J, Schmidt, A M, Neeper, M, Shaw, A, Migheli, A, and Stern, D. Survey of the distribution of a newly-characterized receptor for AGEs in tissues. Am. J. Pathol. 143:1699–1712, 1993.
11. Abel M, Ritthaler U, Zhang Y, Deng Y, Schmidt A M, Greten J, Sernau T, Wahl P, Andrassy K, Ritz E, Stern D, and Nawroth P P. Expression of receptors for advanced glycosylated endproducts in renal disease. Nephrology, Dialysis and Transplantation 10:1662–1667, 1995.
12. Soulis T, Thallas V, Youssef S, Gilbert R E, Mcwilliam B G, Murray-McIntosh R P, Cooper M E. Advanced glycation endproducts and their receptors co-localize in rat organs susceptible to diabetic microvascular injury. Diabetologia 40:619–628, 1997.
13. Schmidt, A. M., S D Yan, and D. Stern. The Dark Side of Glucose (News and Views). Nature Medicine 1:1002–1004, 1995.
14. Yan, S-D, Schmidt, A-M, Anderson, G, Zhang, J, Brett, J, Zou, Y-S, Pinsky, D, and Stern, D. Enhanced cellular oxidant stress by the interaction of advanced glycation endproducts with their receptors/binding proteins. J. Biol. Chem. 269:9889–9897, 1994.
15. Schmidt, A-M, Yan, S-D, Brett, J, Mora, R, Nowygrod, R, and Stern D. Regulation of mononuclear phagocyte migration by cell surface binding proteins for advanced glycosylation endproducts. J. Clin. Invest. 92:2155–2168, 1993.
16. Wautier, J L, Chappey, O, Wautier, M P, Hori, O, Stern, D, and Schmidt A M. Receptor-mediated endothelial dysfunction in diabetic vasculopathy: sRAGE blocks hyperpermeability. J. Clin. Invest. 97:238–243, 1996.
17. Miyata, T., Hori, O, Zhang, J H, Yan, S D, Ferran, L, Iida, Y, and Schmidt, A M. The Receptor for Advanced Glycation Endproducts (RAGE) mediates the interaction of AGE-b$^2$-Microglobulin with human mononuclear phagocytes via an oxidant-sensitive pathway: implications for the pathogenesis of dialysis-related amyloidosis. J. Clin. Invest. 98:1088–1094, 1996.
18. Schmidt, A-M, Hasu, M, Popov, D, Zhang, J-H, Chen, J, Yan, S-D, Brett, J, Cao, R, Kuwabara, K, Gabriela, C, Simionescu, N, Simionescu, M, and Stern D. Receptor for advanced glycation endproducts (AGEs) has a central role in vessel wall interactions and gene activation in response to circulating AGE proteins. PNAS(USA) 91:8807–8811, 1994.

19. Schmidt, A M, Hori, O, Chen, J, Brett, J, and Stern, D. AGE interaction with their endothelial receptor induce expression of VCAM-1: a potential mechanism for the accelerated vasculopathy of diabetes. J. Clin. Invest. 96:1395–1403, 1995.

20. Lander, H. L., Tauras, J. M., Ogiste, J. S., Moss, R. A., and A. M. Schmidt. Activation of the Receptor for Advanced Glycation Endproducts triggers a MAP Kinase pathway regulated by oxidant stress. J. Biol. Chem. 272:17810–17814, 1997.

21. Park, L., Raman, K. G., Lee, K. J., Yan, L., Ferran, L. J., Chow, W. S., Stern, D., and Schmidt, A. M. Suppression of accelerated diabetic atherosclerosis by soluble Receptor for AGE (sRAGE). Nature Medicine 4:1025–1031, 1998.

22. Wu J, Rogers L, Stern D, Schmidt A M and Chiu D T W. The soluble receptor for Advanced Glycation Endproducts (sRAGE) ameliorates impaired wound healing in diabetic mice. Plastic Surgery Research Council, Abstract #77, p. 43, 1997.

23. Wautier J L, Chappey O, Wautier M P, Boval B, Stern D and A M Schmidt. Interaction of diabetic erythrocytes bearing advanced glycation endproducts with the endothelial receptor RAGE induces generation of reactive oxygen intermediates and cellular dysfunction. Circ. 94 (8):#4139, 1996.

24. Reddy, S., Bichler, J., Wells-Knecht, K. J., Thorpe, S. R. and Baynes, J. W. $N^e$-(Carboxymethyl)lysine is a dominant Advanced Glycation Endproduct (AGE) antigen in tissue proteins. Biochemistry 34:10872–10878, 1995.

25. Schleicher, E. D., Wagner, E., and Nerlich, A. G. Increased accumulation of the glycoxidation product $N^e$-(Carboxymethyl)lysine in human tissues in diabetes and aging. J. Clin. Invest. 99:457–468, 1997.

26. Fu, M-X., Requena, J. R., Jenkins, A. J., Lyons, T. J., Baynes, J. W., and Thorpe, S. R. The Advanced Glycation Endproduct, $N^e$-(Carboxymethyl)lysine is a product of both lipid peroxidation and glycoxidation reactions. J. Biol. Chem. 271:9982–9986, 1996.

27. Horie, K., Miyata, T., Maeda, K., Miyata, S., Sugiyama, S., Sakai, H., Van Ypersele de Strihou, C., Monnier, V. M., Witztum, J. L., and Kurokawa, K. Immunohistochemical colocalization of glycoxidation products and lipid peroxidation products in diabetic renal glomerular lesions: implications for glycoxidative stress in the pathogenesis of diabetic nephropathy. J. Clin. Invest. 100:2995–3004, 1997.

28. Sell, D. R., and Monnier, V. M. Structure elucidation of a senescence cross-link from human extracellular matrix. J. Biol. Chem. 264:21597–21602, 1989.

29. Portero-Otin, M., Nagaraj, R. H., and Monnier, V. M. Chromatographic evidence for pyrraline formation during protein glycation in vitro and in vivo. Biochim. Biophys. Acta 1247:74–80, 1995.

30. Shamsi, F. A., Partal, A., Sady, C., Glomb, M. A., and Nagaraj, R. H. Immunological evidence for methylglyoxal-derived modifications in vivo. J. Biol. Chem. 273:6928–6936, 1998.

31. Schmidt, A. M., Yan, S. D., and Stern, D. The V-Domain of Receptor for Advanced Glycation Endproducts (RAGE) mediates binding of AGEs: a novel target for therapy of diabetes. Circ. (Suppl)., 96:#194, p. I-37, 1997.

32. Marui, N. Offermann, M., Swerlick, R., Kunsch, C. Raosen, C. Ahmad, M., Alexander, R., and Medford, R. VCAM-1 gene transcription and expression are regulated through an oxidant-sensitive mechanism in human vascular endothelial cells. J. Clin. Invest. 92:1866–1874.

33. Schreiber, E., Matthias, P., Muller, M., and Schaffner, W. Rapid detection of octamer binding proteins with "mini-extracts," prepared from a small number of cells. Nucleic Acids Research 17:6419, 1989.

34. Li, J., and Schmidt, A. M. Characterization and functional analysis of the promoter of RAGE, the Receptor for Advanced Glycation Endproducts. J. Biol. Chem. 272:16498–16506, 1997.

Carpenter, et al. (1971) Toxicol. Appl. Pharmacol., 18:35–40.

What is claimed is:

1. A method for determining whether a compound is capable of inhibiting the interaction of a peptide with a receptor for advanced glycation end product (RAGE), which comprises:
   (a) admixing:
      (i) the peptide, wherein amino groups of the peptide are inactivated by chemical derivitization,
      (ii) RAGE or a fragment thereof which is capable of binding the peptide, and
      (iii) the compound;
   (b) determining the amount of the peptide bound to RAGE or the fragment thereof, and
   (c) comparing the amount of bound peptide determined in step (b) with the amount determined when the peptide is admixed with RAGE or a fragment thereof in the absence of the compound, thereby determining whether the compound is capable of inhibiting the interaction of the peptide with RAGE or fragment thereof, wherein a reduction in the amount of binding in the presence of the compound indicates that the compound is capable of inhibiting the interaction.

2. The method of claim 1, wherein the fragment of RAGE is the V-domain.

3. The method of claim 1, wherein the fragment of RAGE has the amino acid sequence of the V-domain sequence of RAGE.

4. The method of claim 1, wherein the RAGE or fragment thereof of step (a)(ii) is synthetic.

5. The method of claim 1, wherein the compound comprises a fragment of naturally occuring soluble receptor for advanced glycation endproduct (sRAGE).

6. The method of claim 1, wherein the compound is an organic molecule.

7. The method of claim 1, wherein the compound is a polypeptide, a nucleic acid, or an inorganic chemical.

8. The method of claim 1, wherein the compound is an antibody or a fragment thereof.

9. The method of claim 8, wherein the antibody is a polyclonal or monoclonal antibody.

10. The method of claim 8, wherein the antibody is humanized, chimeric or primatized.

11. The method of claim 1, wherein the peptide is affixed to a solid surface.

12. The method of claim 1, wherein the RAGE or the fragment thereof is affixed to a solid surface.

13. The method of claim 1, wherein the peptide is detectably labeled.

14. The method of claim 1, wherein the RAGE or the fragment thereof is detectably labeled.

15. The method of claim 13 or 14, wherein the detectable label comprises fluorescence, biotin, or radioactivity.

* * * * *

UNITED STATES PATENT AND TRADEMARK OFFICE
CERTIFICATE OF CORRECTION

PATENT NO. : 6,753,150 B2  Page 1 of 1
APPLICATION NO. : 09/166649
DATED : June 22, 2004
INVENTOR(S) : Ann Marie Schmidt and David Stern It is certified that error appears in the above-identified patent and that said Letters Patent is hereby corrected as shown below:

In claim 1, column 22, lines 17-18: "is capable of inhibiting the interaction of a peptide" should read -- inhibits the interaction of a carboxymethyl-lysine-modified advanced glycation endproduct (AGE) --

In claim 1, column 22, lines 22-23: "the peptide, wherein amino groups of the peptide are inactivated by chemical derivatization," should read -- the carboxymethyl-lysine-modified AGE --

In claim 1, column 22, lines 24-25: "is capable of binding the peptide" should read -- binds to the carboxymethyl-lysine-modified AGE --

In claim 1, column 22, line 29: "peptide" should read -- AGE --

In claim 1, column 22, line 30: "peptide" should read -- AGE --

In claim 1, column 22, line 33: "is capable of inhibiting" should read -- inhibits --

In claim 1, column 22, line 34: "peptide" should read -- AGE --

In claim 1, column 22, lines 36-37: "is capable of inhibiting" should read -- inhibits --

In claim 11, column 22, line 58: "peptide" should read -- AGE --

In claim 13, column 22, line 62: "peptide should read -- AGE --

Signed and Sealed this

Sixteenth Day of December, 2008

JON W. DUDAS
*Director of the United States Patent and Trademark Office*